United States Patent [19]

Wright et al.

[11] Patent Number: 4,520,827

[45] Date of Patent: Jun. 4, 1985

[54] NMS AIDED CONTINUOUS PASSIVE MOTION APPARATUS

[75] Inventors: Thomas C. Wright, New Brighton; Stephen H. Ober, Chaska, both of Minn.

[73] Assignee: EMPI, Inc., Fridley, Minn.

[21] Appl. No.: 578,470

[22] Filed: Feb. 9, 1984

[51] Int. Cl.³ ............................................. A61N 1/36
[52] U.S. Cl. ............................................. 128/423 W
[58] Field of Search ...................... 128/24.5, 421, 422, 128/423 W, 707, 782; 3/1.2, 1.1; 272/70, 70.3, 73; 340/407

[56] References Cited

U.S. PATENT DOCUMENTS

| | | | |
|---|---|---|---|
| 2,002,586 | 5/1935 | Ryberg, Jr. ........................ | 128/24.5 |
| 3,449,769 | 6/1969 | Mizen ................................ | 3/1.2 |
| 3,911,910 | 10/1975 | Oesau ............................... | 3/1.1 |
| 4,392,496 | 7/1983 | Stanton ............................. | 128/423 W |
| 4,421,336 | 12/1983 | Petrofsky et al. ................. | 3/1.1 |
| 4,480,830 | 11/1984 | Petrofski et al. ................. | 128/423 W |

Primary Examiner—William E. Kamm
Attorney, Agent, or Firm—Kinney & Lange

[57] ABSTRACT

A continuous passive motion (CPM) apparatus mobilizes the knee joint of a patient's leg. In order to achieve total extension of the leg, the CPM apparatus pauses each time the extension end position is reached. A neuro-muscular stimulator (NMS) is enabled to provide stimulation to the patient's quadriceps muscle to effect a total extension of the leg. At the end of the pause interval, the NMS turns off, and the CPM resumes motion.

24 Claims, 3 Drawing Figures

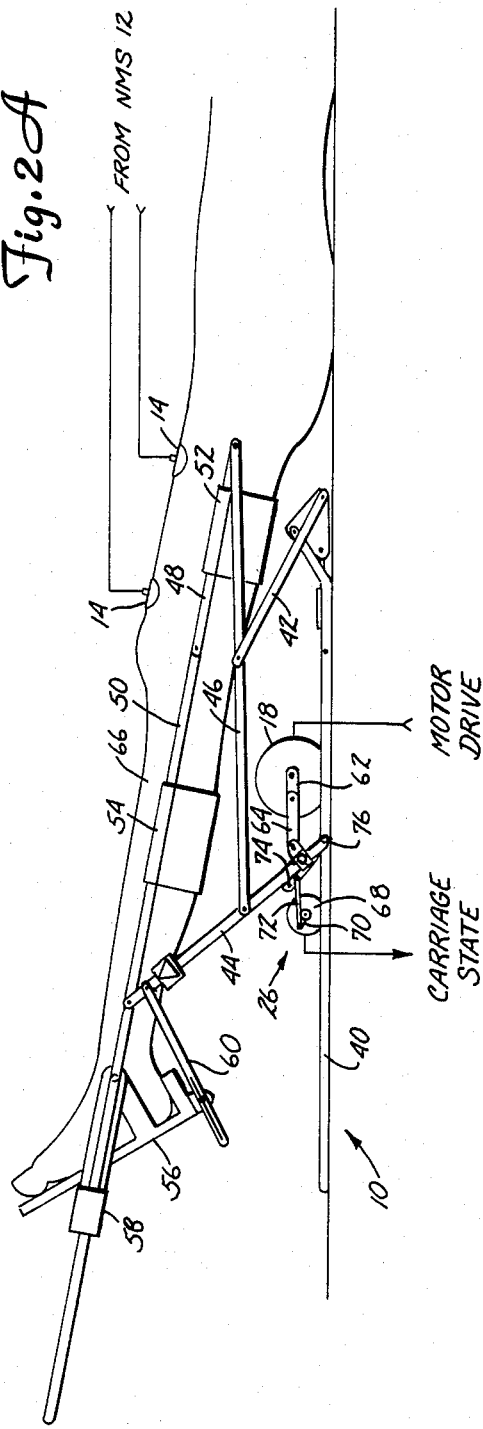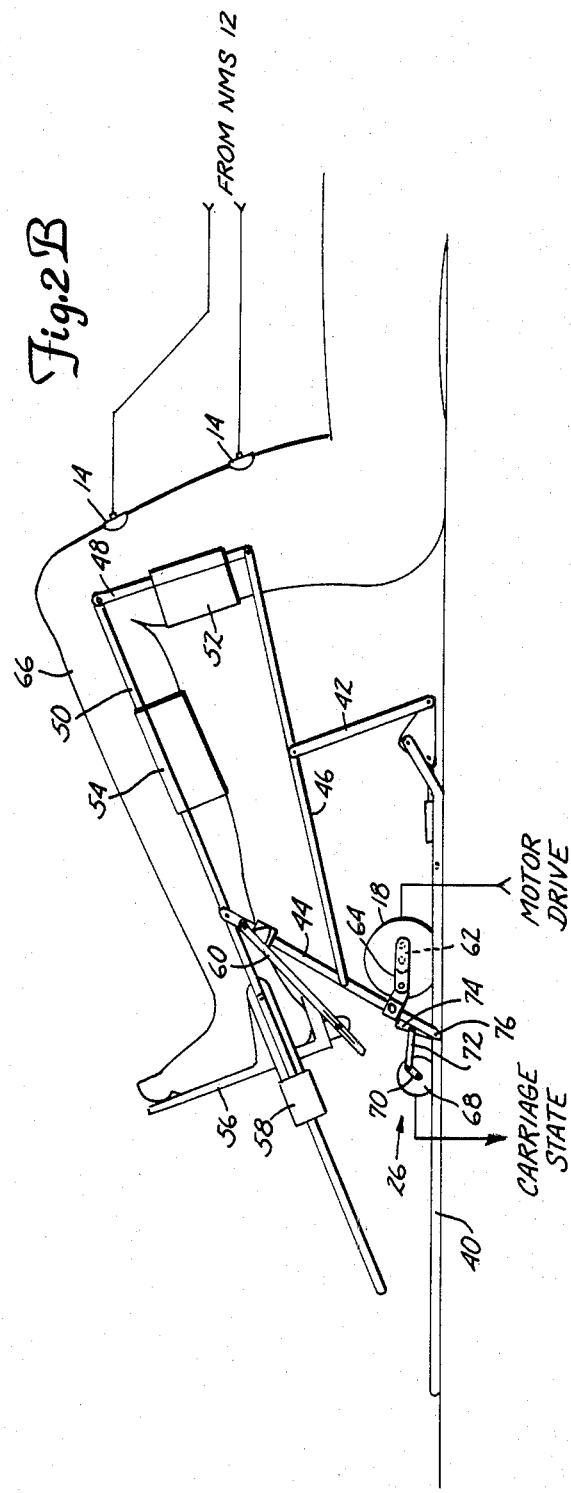

NMS AIDED CONTINUOUS PASSIVE MOTION APPARATUS

REFERENCE TO COPENDING APPLICATION

Reference is made to the following copending application filed on even date and assigned to the same assigee as the present application:

"Orthosis for Leg Movement with Virtual Hip Pivot", J. Berner et al, Ser. No. 578,731.

BACKGROUND OF THE INVENTION

1. Field of the Invention

This invention relates to continuous passive motion apparatus for mobilizing the knee joint of the patient's leg.

2. Description of the Prior Art

In recent years, there has been an increasing awareness of the advantages of mobilization of joints as a part of the orthopedic care which follows an injury, an illness, or a surgical procedure. A joint can stiffen rapidly as a result of immobilization, and in many cases extensive therapy is required in order to regain full use of the joint after it has stiffened.

Active motion of a joint occurs when the patient has sufficient muscle strength to flex or extend the limb without need for external applied force. In contrast, passive motion of a joint involves the use of an external force to flex and extend the limb to induce motion. Continuous passive motion of a joint following injury, illness or surgery has been found to reduce post-operative pain, decrease adhesions, decrease muscle atrophy, and enhance the speed of recovery, while minimizing other risks of immobilization such as venous stasis, thromboembolism and post-traumatic osteopenia.

Continuous passive motion (CPM) devices developed in the past have, in general, included a base or frame, a femur support which supports the upper part of the leg, a tibia support which supports the lower part of the leg, and a drive system. The femur support typically is pivoted with respect to the base while while the tibia support pivots with respect to the femur support and is supported above the frame. Examples of this type of device are shown in the Ragon et al U.S. Pat. No. 3,450,132, the Bimler U.S. Pat. No. 3,717,144 and the Pecheux U.S. Pat. No. 4,323,060.

SUMMARY OF THE INVENTION

The present invention is based upon the recognition that in the postoperative recovery stage of a knee patient, it is both important and difficult to effect a total extension of the leg. This extension occurs through the action of the quadriceps muscle. Often a patient will not willingly activate this muscle, and the leg will not extend fully. A continuous passive motion device cannot substitute for this muscular action.

In the present invention, a continuous passive motion device moves the patient's leg through a reciprocal cycle between a flexion end position in which an angle between the femur and tibia is at a minimum and an extension end position in which the angle between the femur and tibia is at a maximum. The present invention further includes neuro-muscular stimulation (NMS) means for providing electrical stimulation to the patient's quadriceps muscle, and control means which coordinates the operation of the CPM device and the NMS means in order to effect total extension of the leg.

In the present invention, the control means stops the CPM device when the extension end position has been reached and enables the NMS means to stimulate the patient's quadriceps muscle during a pause interval in which the CPM is stopped, thus ensuring the knee is fully extended. At the end of the pause interval, the NMS means is turned off by the control means, and the CPM device is enabled to resume its motion. The pause interval and electrical stimulation of the quadriceps muscle is repeated each time the CPM device reaches the extension end position.

BRIEF DESCRIPTION OF THE DRAWINGS

FIGS. 2A and 2B are side elevational views of a preferred embodiment of the present invention, illustrating the flexion and extension end positions, respectively.

DETAILED DESCRIPTION OF THE PREFERRED EMBODIMENTS

Figure 1:
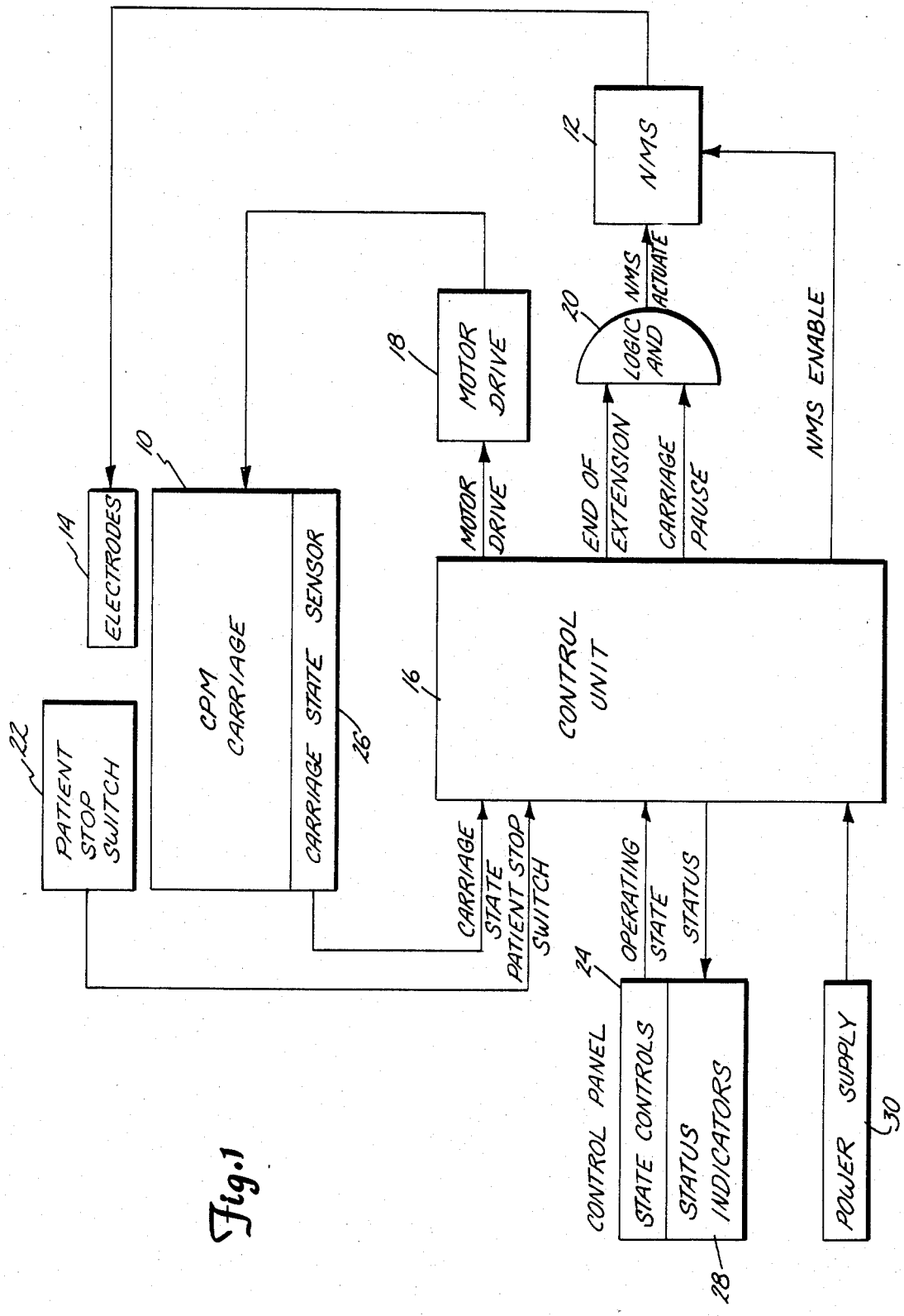
FIG. 1 is an electrical block diagram of the present invention.

The block diagram shown in FIG. 1 illustrates a preferred embodiment of the present invention, in which therapy for postoperative recovery of a knee of a patient is enhanced by the coordinated use of continuous passive motion and neuro-muscular stimulation. The apparatus shown in FIG. 1 includes CPM carriage 10 which causes continuous passive motion of the patient's leg (and particularly the knee joint of that leg) and neuro-muscular stimulator (NMS) 12 which supplies electrical stimulation to the quadriceps muscle of the patient's leg through electrodes 14 which are applied to the patient's leg. Control unit 16 controls operation of motor drive 18 (which moves CPM carriage 10) and controls NMS 12 through logic AND gate 20. Control unit 16 receives input signals from patient stop switch 22, control panel state controls 24, and carriage state sensor 26, and provides status indication output signals to status indicators 28. Power supply 30 provides electrical power to control unit 16.

During normal operation, control unit 16 controls motor drive 18 to cause CPM carriage 10 to move the patient's leg in a reciprocal fashion between a flexion end position and an extension end position. The flexion end position is the position at which the angle between the femur and tibia of the patient's leg is at a minimum. The extension end position is the position at which the angle between the femur and tibia is at a maximum.

Control unit 16 controls the operation of motor drive 18 based upon Operating State input signals from state controls 24, a Patient Stop Switch signal from patient stop switch 22, and Carriage State input signals from carriage state sensor 26. The Operating State input signals from state controls 24 select the operating time cycle of CPM carriage 10 (and thus the speed of motor drive 18), select NMS 12 to be enabled, select whether a pause at the extension end position is desired if NMS is not enabled, and select the flexion end position and the extension end position. The Patient Stop Switch input signal allows the patient to stop and restart CPM carriage 10 and NMS 12 at any time, and thus provides an additional safety feature for the apparatus.

As discussed previously, it is both important and difficult to effect a total extension of the leg during post-operative recovery from knee surgery. A total extension of the leg means that the extension end position achieved by CPM carriage 10 should result in an angle between the femur and tibia of about 180°. This total extension, however, requires the action of the quadriceps muscle of the patient's leg. Often the patient will not willingly active the quadriceps muscle and will unconsciously resist the action of CPM carriage 10 so that the leg does not extend fully. CPM carriage 10 should not substitute for the action of the quadriceps muscle in achieving the desired total extension of the leg due to the anatomical limit of knee extension.

In the present invention, control unit 16 monitors the position of CPM carriage 10 through carriage state sensor 26 and provides a pause in the Motor Drive signal to motor drive 18 when the extension end position of CPM carriage 10 is reached and NMS is desired. The pause feature may be enabled with or without the NMS 12 being activated. However, if NMS 12 is enabled (by an NMS Enable signal), the pause feature will be activated. The pause interval during which no Motor Drive signal is supplied is either a preset duration (for example, ten seconds) or a selectable duration (for example, two seconds to twenty seconds) which is selectable through state controls 24.

Control unit 16 provides an End-Of-Extension signal and a Carriage Pause signal to logic AND gate 20, and the NMS Enable signal to NMS 12. The End-Of-Extension signal is derived by control unit 16 from the Carriage State Input signal provided by carriage state sensor 26, and indicates that CPM carriage 10 is at or near the extension end position. The Carriage Pause signal defines the pause interval during which motor drive 18 is disabled. When both the End-Of-Extension signal and Carriage Pause signal are present, AND gate 20 provides an NMS Actuate signal to NMS 12. If the NMS Enable signal is also present, the NMS Actuate signal turns on NMS 12, which provides an electrical neuro-muscular stimulation to the quadriceps muscle of the patient's leg through electrodes 14. At the end of the pause interval, the Carriage Pause signal changes state, and AND gate 20 discontinues the NMS Actuate signal. This turns off NMS 12, thus discontinuing the electrical neuro-muscular stimulation to the quadriceps muscle. At the end of the pause interval, control unit 16 again supplies the Motor Drive signal to motor drive 18, which allows CPM carriage 10 to resume its reciprocal motion. This cycle repeats itself each time CPM carriage 10 reaches the extension end position as indicated by the Carriage State signal from carriage state sensor 26. The total number of cycles or the total period of time during which the apparatus operates is, in some embodiments, selectable through state controls 24.

The apparatus of the present invention is applicable to a wide variety of different CPM carriages. FIGS. 2A and 2B illustrate operation of the present invention with an embodiment of CPM carriage 10 which is described in further detail in a copending application entitled "Orthosis for Leg Movement with Virtual Hip Pivot" by John M. Berner, filed on even date with this application and assigned to the same assignee as the present application.

In the embodiment shown in FIGS. 2A and 2B, CPM carriage 10 includes frame 40, a pair of parallel rearward support links 42, a pair of parallel forward support links 44, a pair of parallel drag links 46, a pair of parallel femur support members 48, a pair of parallel tibia support members 50, thigh support saddle 52, calf support saddle 54, foot support 56, connector 58, and connecting link 60. Links 42, 44 and 46 and support members 48 and 50 form a double four-bar linkage which transmits the drive power supplied from motor drive 18 through crank 62 and link 64 to cause reciprocal movement of leg 66 between the extension end position shown in FIG. 2A and the flexion end position shown in FIG. 2B.

Electrodes 14 shown in FIGS. 2A and 2B are affixed to the skin of leg 66, and are positioned to cause contraction of the quadriceps muscle of leg 66 when an electrical neuro-muscular stimulation signal is received from NMS 12. The contraction of the quadriceps muscle causes extension of leg 66.

In the embodiment shown in FIGS. 2A and 2B, carriage state sensor 26 comprises potentiometer 68 which is connected through links 70 and 72 to arm 74. The Carriage State signal from potentiometer 68 is an analog voltage signal which is proportional to the angular position of arm 74. Forward support links 44 are pivotally connected to frame 40 by pivot shaft 76. Arm 74 is also fixedly connected to pivot shaft 76, so that the angular position of arm 74 follows the angular position of forward support links 44. As a result, the analog Carriage State signal has a magnitude which is representative of the position of CPM carriage 10 in its operating cycle.

In one preferred embodiment, control unit 16 determines the flexion end position and the extension end position based upon a comparison of the magnitude of the Carriage State signal with flexion and extension end point values selected by control panel state controls 24. When each end position is reached, control unit 16 changes the direction of rotation of motor drive 18 to reverse the direction of angular movement of femur and tibia support members 48 and 50.

When CPM carriage 10 is at or very near the extension end position shown in FIG. 2A, control unit provides the End-Of-Extension signal which indicates the proximity of carriage 10 to the extension end position. Control unit 16 then discontinues the Motor Drive signal to motor drive 18, and provides the Carriage Pause signal to AND gate 20, which in turn provides the NMS Actuate signal to NMS 12. Electrodes 14 shown in FIGS. 2A and 2B provide the NMS Stimulation signal to the quadriceps muscle, thus causing full extension of leg 66 as shown in FIG. 2A.

In conclusion, the present invention combines and coordinates the operation of CPM carriage 10 and NMS 12 to increase the therapeutic value during post-operative recovery from knee surgery by overcoming the tendency of a patient to resist total extension of the leg. The pause interval at the extension end position of CPM carriage 10 ensures that the stimulation of the quadriceps muscle by NMS 12 occurs at a time when carriage 10 is at the proper position to achieve maximum therapeutic value for the patient.

Although the present invention has been described with reference to preferred embodiments, workers skilled in the art will recognize that changes may be made in form and detail without departing from the spirit and scope of the invention.

What is claimed is:

1. Apparatus for moving a leg of a patient, comprising:
   continuous passive motion carriage means for supporting the leg through a range of reciprocal angular movement;
   drive means for causing reciprocal angular movement of the carriage means between a flexion end position in which an angle of a knee joint of the leg is at a minimum, and an extension end position in the angle is at a maximum;

neuro-muscular stimulation means for applying electrical stimulation to a quadriceps muscle of the leg;

carriage state sensor means for providing a signal representative of a state of the carriage means within the range of reciprocal angular movement; and control means for controlling the drive means and the neuro-muscular stimulation means to cause the drive means to pause for a predetermined pause interval when the carriage state sensor provides a signal indicating that the carriage means is at the extension end position and enabling the neuro-muscular stimulation means to provide the electrical stimulation to the quadriceps muscle during the pause interval.

2. The apparatus of claim 1 wherein the control means, provides an NMS enable signal to enable operation of the neuro-muscular stimulation means, provides an end-of-extension signal based upon the signal from the carriage state sensor means which indicates that the carriage means is at the extension end position, and provides a carriage pause signal which indicates the presence of the pause interval, and wherein the control means provides an NMS actuate signal to the neuro-muscular stimulation means only when the end-of-extension signal and the carriage pause signal are both present; and wherein the neuro-muscular stimulation means applies electrical stimulation only in response to both the NMS enable signal and the NMS actuate signal.

3. The apparatus of claim 1 and further comprising:
means for providing an input signal to the control means which selects a time duration of the pause interval.

4. The apparatus of claim 1 and further comprising:
patient stop switch means for providing a patient stop switch signal to the control means which causes the control means to stop the drive means and disables the neuro-muscular stimulation means.

5. The apparatus of claim 1 wherein the control means provides a drive signal to the drive means which controls speed of operation of the drive means, and interrupts the drive signal during the pause interval.

6. The apparatus of claim 5 and further comprising:
means for providing an input signal to the control means which selects an operating speed for the drive means.

7. The apparatus of claim 1 and further comprising:
means for providing an input signal to the control means which selects an operating period of the drive means.

8. The apparatus of claim 1 wherein the carriage state sensor means provides the signal with a magnitude which varies as a function of position of the carriage means; wherein the control means compares the magnitude to first and second values representing the flexion end position and the extension end position, respectively, and reverses direction of angular movement of the carriage means when each end position is reached; and wherein the apparatus further comprises means for selecting the first and second values.

9. An apparatus for moving a leg of a patient comprising:
a first support for supporting an upper part of the leg;
a second support pivotally connected to the first support for supporting a lower part of the leg;
drive means for causing reciprocal angular movement of the first and second supports between a flexion end position in which an angle between the first and second supports is at a minimum and an extension end position in which the angle is at a maximum;
neuro-muscular stimulation means for applying electrical stimulation to a quadriceps muscle of the leg; and
control means for pausing the drive means and enabling the neuro-muscular stimulation means during a pause interval when the first and second supports are at the extension end position.

10. The apparatus of claim 9 and further comprising:
means for providing a position signal which indicates when the first and second supports are proximate the extension end position; and
wherein the control means pauses the drive and enables the neuro-muscular stimulation means in response to the position signal.

11. The apparatus of claim 10 and further comprising:
means for providing an input signal to the control means which selects a time duration of the pause interval.

12. The apparatus of claim 10 wherein the position signal has a magnitude which is a function of angular position of the first and second supports; wherein the control means compares the position signal to first and second values representing the flexion and extension end positions, respectively, and reverses direction of angular movement of the first and second supports when each end position is reached; and wherein the apparatus further comprises means for selecting the first and second values.

13. The apparatus of claim 9 and further comprising:
patient stop switch means for providing a patient stop switch signal to the control means which causes the control means to stop the drive means and disables the neuro-muscular stimulation means.

14. The apparatus of claim 9 wherein the control means provides a drive signal to the drive means which controls speed of operation of the drive means, and interrupts the drive signal during the pause interval.

15. The apparatus of claim 14 and further comprising:
means for providing an input signal to the control means which selects an operating speed for the drive means.

16. The apparatus of claim 9 and further comprising:
means for providing an input signal to the control means which selects an operating period of the drive means.

17. An apparatus for moving a leg of a patient, the apparatus comprising:
a frame;
first and second supports for supporting upper and lower parts of the leg, respectively;
means for connecting the first support for relative angular movement with respect to the frame;
means for pivotally connecting the first and second supports for relative angular movement;
drive means for causing reciprocal movement of the first and second supports between a flexion end position in which a first angle between the first support and the frame is a maximum and a second angle between the first and second supports is a minimum, and an extension end position in which the first angle is a minimum and the second angle is a maximum;

neuro-muscular stimulation means connected to the leg for applying electrical stimulation to a quadriceps muscle of the leg; and control means for controlling the drive means and the neuro-muscular stimulation means to cause the drive means to pause for a predetermined pause interval in the reciprocal movement when the first and second supports are at the extension end position and to cause the neuro-muscular stimulation means to provide the electrical stimulation to the quadriceps muscle during the pause interval.

18. The apparatus of claim 17 and further comprising:
means for providing a position signal which indicates when the first and second supports are proximate the extension end position; and
wherein the control means pauses the drive and enables the neuro-muscular stimulation means in response to the position signal.

19. The apparatus of claim 18 and further comprising:
means for providing an input signal to the control means which selects a time duration of the pause interval.

20. The apparatus of claim 18 wherein the position signal has a magnitude which is a function of angular position of the first and second supports; wherein the control means compares the position signal to first and second values representing the flexion and extension end positions, respectively, and reverses direction of angular movement of the first and second supports when each end position is reached; and wherein the apparatus further comprises means for selecting the first and second values.

21. The apparatus of claim 17 and further comprising:
patient stop switch means for providing a patient stop switch signal to the control means which causes the control means to stop the drive means and disables the neuro-muscular stimulation means.

22. The apparatus of claim 17 wherein the control means provides a drive signal to the drive means which controls speed of operation of the drive means, and interrupts the drive signal during the pause interval.

23. The apparatus of claim 22 and further comprising:
means for providing an input signal to the control means which selects an operating speed for the drive means.

24. The apparatus of claim 17 and further comprising:
means for providing an input signal to the control means which selects an operating period of the drive means.

* * * * *